United States Patent [19]

Eveleigh

[11] Patent Number: 5,270,193

[45] Date of Patent: * Dec. 14, 1993

[54] IMMOBILIZATION OF BIOMOLECULES ON PERFLUOROCARBON SURFACES

[75] Inventor: John W. d. Eveleigh, Amherst, N.H.

[73] Assignee: E. I. DuPont de Nemours and Company, Wilmington, Del.

[*] Notice: The portion of the term of this patent subsequent to Dec. 5, 2008 has been disclaimed.

[21] Appl. No.: 785,887

[22] Filed: Oct. 24, 1991

Related U.S. Application Data

[63] Continuation-in-part of Ser. No. 428,154, Oct. 27, 1989, abandoned.

[51] Int. Cl.$^5$ .................. C12N 11/06; C12N 11/08; G01N 33/549; G01N 33/545
[52] U.S. Cl. .................. 435/181; 435/180; 436/531; 436/532; 530/815; 530/816
[58] Field of Search ............ 435/174, 180, 181; 436/518, 531, 532; 530/811, 815, 816

[56] References Cited

U.S. PATENT DOCUMENTS

| | | | |
|---|---|---|---|
| 3,639,516 | 2/1972 | Sarfaty et al. | 260/818 R |
| 3,700,609 | 10/1972 | Tregear et al. | 260/2.5 R |
| 4,035,316 | 7/1977 | Yen et al. | 260/2.5 |
| 4,105,598 | 8/1978 | Yen et al. | 521/53 |
| 4,177,038 | 12/1979 | Biebricher et al. | 8/192 |
| 4,179,337 | 12/1979 | Davis et al. | 435/181 |
| 4,267,273 | 5/1981 | Smith | 435/44 |
| 4,642,285 | 2/1984 | Halbert et al. | 435/7 |
| 4,885,250 | 12/1989 | Eveleigh et al. | 435/181 |
| 4,954,444 | 9/1990 | Eveleigh et al. | 435/181 |
| 5,079,155 | 1/1992 | Cox et al. | 435/181 |

FOREIGN PATENT DOCUMENTS

| | | |
|---|---|---|
| 0198395 | 10/1986 | European Pat. Off. . |
| 269092 | 6/1988 | European Pat. Off. . |
| 61-218946 | 3/1985 | Japan . |
| 61-155959 | 7/1986 | Japan . |
| 61-155960 | 7/1986 | Japan . |

OTHER PUBLICATIONS

De Miguel et al., Chromatraphia, vol. 24, 849 853 (1987).

Primary Examiner—David M. Naff

[57] ABSTRACT

Biomolecules such as a ligand or binder for the ligand are securely but reversibly attached to a perfluorocarbon carrier with a water soluble polymer, a perfluorocarbon anchoring group and optionally a linker group. The order of steps for carrying out the attachment can vary. For example, the biomolecule is covalently attached to the polymer followed by covalently attaching the anchoring group and attaching the resultant product to the carrier. Alternatively, the anchoring group is covalently attached to the polymer followed by attaching the resultant product to the carrier and then covalently attaching a biomolecule to the polymer. The polymer may be starch, dextran, agarose, polyethylene glycol or polyvinyl alcohol. An attached ligand or binder for the ligand is useful in affinity separations and immunoassays.

18 Claims, No Drawings

IMMOBILIZATION OF BIOMOLECULES ON PERFLUOROCARBON SURFACES

CROSS-REFERENCE TO RELATED APPLICATIONS

This application is a continuation-in-part of U.S. Ser. No. 07/428,154, filed Oct. 27, 1989, now abandoned.

TECHNICAL FIELD

This invention is related to the attachment of biomolecules to carriers and more specifically to the secure noncovalent attachment of biomolecules to perfluorocarbon carriers utilizing modified water soluble polymers.

BACKGROUND ART

A biomolecule may be defined as any molecule or substance of biological interest. The biomolecule may have its own biological activity or simply be engaged in a biological reaction. The biomolecule can be a ligand, binder, protein, enzyme, antigen, antibody, nucleic acid, vitamin, dye, substrate, cofactor, etc. Immobilized biomolecules have been widely used for a variety of applications including bioaffinity separations, immunoassays, bioreactors and biosensors. One of the most difficult problems in immobilizing a biomolecule to a solid or liquid carrier is achieving the efficiency and stability of attachment. In an attempt to overcome this difficulty, the covalent attachment technique, involving derivatization of the carrier surface to chemically couple with a biomolecule, has been commonly used. The biomolecule can be immobilized directly or immobilized via a linker. However, this approach has well known disadvantages including introduction of reactive groups to the carrier surface often leading to increased nonspecific binding, significant loss of reactivity of the immobilized biomolecule, and permanent attachment of the biomolecule preventing it from being recovered for re-use. Recoverability is an important aspect of immobilization when the biomolecule is a scarce or very expensive reagent.

The general covalent attachment methods will not be reviewed in this application but those employing a perfluorocarbon polymer-based carrier will be addressed. Halbert et al., U.S. Pat. No. 4,642,285, issued Feb. 10, 1987, disclose a method of covalently attaching proteins such as an antibody onto an insoluble member. To effect this bonding, the insoluble member used must be provided with reactive groups or sites capable of reacting with the specific antibody used. The insoluble member disclosed in this reference is a commercially available material known as PROTAPOL DI/1 from Imperial Chemical Industries of Australia and New Zealand (ICIANZ). The material is available in a disc form and comprises a polytetrafluoroethylene (PTFE) backbone having isothiocyanopolystyrene groups grafted uniformly over its surface. The method provides a means for directly immobilizing macromolecules via the reactive groups introduced to the chemically inert perfluorocarbon solid carrier. However, the method does not take advantage of the inherent low nonspecific binding properties of the PTFE polymer and suffers from the known disadvantages described above.

Tregear et al., U.S. Pat. No. 3,700,609, issued Oct. 24, 1972, also disclose a graft copolymer such as those described by Halbert et al. The copolymer comprises a polymeric backbone, for example, PTFE, onto which is grafted a different copolymerizable comonomer having substituent groups capable of forming a chemical bond with a protein. A preferred protein reactive group is the isothiocyanate group or the chloromethyl group. Again, the method is for a direct covalent attachment of biomolecules onto the surface of the copolymer having reactive groups.

Sarfaty et al., U.S. Pat. No. 3,639,516, issued Feb. 1, 1972, also disclose a graft copolymer comprising a polymeric nucleus such as PTFE or polytrifluoromonochloro ethylene polymer, and surface grafted on to it copolymeric side chains comprising a copolymer such as styrene or substituted styrene. The difference is that the graft copolymer in this patent is designed to have specific reactivities toward carbonylic steroids. The invention describes the use of such a copolymer for separation of carbonylic steroids.

Yen et al., U.S. Pat. No. 4,035,316, issued Jul. 12, 1977, describe a method for isolation of specific cells by density gradient centrifugation. The technique involves labeling of cells to be separated with lectin or cell-specific antibody attached to microspheres. The microspheres comprise a biocompatible copolymer, for example, a hydroxy or amine substituted acrylic monomer such as hydroxyethyl methacrylate with a light or dense comonomer such as a fluoromonomer. Here, the fluoromonomer such as trifluoroethyl methacrylate, hexafluoroisopropyl methacrylate or pentafluorostyrene in the generation of microspheres is used to provide a density adequate for separation of the labeled cells by sedimentation or centrifugation techniques. The same method is also disclosed in a Divisional of the above patent, U.S. Pat. No. 4,105,598, issued Aug. 8, 1978.

Biebricher et al., U.S. Pat. No. 4,177,038, issued Dec. 4, 1979, describe a method to permit biologically active matter to be bonded to an insoluble vehicle in such a manner that the capability of the biological substance of interacting with another biological substance is not impaired. The method uses polyethylene glycol as a linker to extend the distance between a biological material and the carrier. Similarly, Davis et al., U.S. Pat. No. 4,179,337, issued Dec. 18, 1989, disclose a method of coupling polypeptides to polyethylene glycol or polypropylene glycol to provide physiologically active non-immunogenic water soluble compositions for injection.

In general, the use of polyglycols imparts protection to sensitive biologically active molecules but fails to provide an adequate number of functional groups to which to attach other chemical entities.

Another commonly used method of immobilization is a simple adsorption technique. The major disadvantage of this approach is the weakness of the attachment. Adsorption involves complex nonspecific hydrophobic, charge and Van der Waals interactions between the biomolecule, reaction medium and surface of the carrier. Thus, the efficiency of attachment or reactivity of the immobilized biomolecule is rather unpredictable. Furthermore, due to the nonspecific nature of interactions, the problem of nonspecific binding is apparent. The immobilized biomolecule often leaches off during use and is sensitive to reaction conditions such as pH, ionic strength and buffer type.

A novel method for noncovalent attachment of an affinity ligand or binder onto a solid or liquid perfluorocarbon carrier has been disclosed in pending applications, U.S. Ser. Nos. 07/032,642, filed Mar. 31, 1987, now abandoned; 07/134,026, filed Dec. 17, 1987, now abandoned; 07/020,808, filed Mar. 2, 1987, now U.S. Pat. No. 4,885,250, issued Dec. 5, 1989, and 07/134,028, filed Dec. 17, 1987, now U.S. Pat. No. 4,954,444, issued Sep. 4, 1990. U.S. Ser. No. 07/032,642 is a continuation-in-part of 06/863,607, filed May 15, 1986; both have since been abandoned. The immobilization technique employs chemical modification of a ligand or binder to effect a specific interaction between the ligand or binder with the carrier. The ligand or binder is modified to introduce a perfluoroalkyl group which anchors onto the perfluorocarbon surface of the carrier by the strong fluorophilic interactions. The invention in these applications offers a way to securely but reversibly immobilize the ligand or binder onto a chemically inert surface having low nonspecific binding properties. While the method is widely applicable for preparation of affinity supports or immobilized enzymes, it is most effective with the ligand or binder having multiple reactive groups for substitution with multiple perfluoalkyl anchoring groups.

A small ligand such as a hapten or a dye molecule often has only one reactive group. Perfluoroalkylation of such ligands will anchor onto a perfluorocarbon surface but the attachment is not as secure, thus resulting in potential desorption of the ligands upon change in pH or ionic strength. It is an object of this invention to provide an improved means especially useful for securely attaching small biomolecules. In the case of enzymes, perfluoroalkylation at multiple sites may lead to a reduction in specific activity. Furthermore, immobilization onto a carrier through the multiple anchoring groups may enhance unfolding of the protein resulting in a severe reduction in specific activity. It is another object of this invention to provide an improved means useful for securely attaching enzymes or other proteins having biological activity without compromising their reactivity.

Smith et al., U.S. Pat. No. 4,267,273, issued May 12, 1981, disclose a method for recovering enzymes from the reaction medium for re-use. To accomplish the separation, an enzyme is chemically modified to attach sufficient non-polar groups, such that on contacting the preparation in aqueous media with an inert water-immiscible liquid, the preparation becomes associated with said water-immiscible liquid separated from the aqueous medium. Sometimes, it is not possible to attach non-polar groups directly to the enzyme without significantly reducing its activity. Thus, it is often preferable to prepare the enzyme bonded to or adsorbed on a polymeric support, which may then carry multiple non-polar groups. The method is an improvement over the conventional use of immobilized enzymes on an insoluble solid support or of water-soluble enzyme-polymer complexes obviating the need to filter or centrifuge for recovery of the enzyme. However, the invention does not teach how to improve attachment of a protein such as an enzyme to the surface of a carrier.

A publication by De Miguel et al., Chromatographia, Vol 24, 849–853, 1987, reports that the specific retention of perfluorinated(PF) compounds on PF stationary phases grows exponentially by increasing the chain length and the number of chains within the same compound. A strong cooperative effect is observed with the multi-strand compounds. For example, the double strand bis 1,2 (heptafluorobutanoyl-oxyl) butane having two three-carbon backbone perfluoro groups is more retained than the single strand (tridecafluoroheptanoyloxyl) butane although the number of fluorinated carbon atoms is the same. Based on these observations, the authors speculate that the tremendous retention power introduced by these multi-strand compounds should allow the dynamic anchoring of biomolecules. However, this aspect of the invention has been fully demonstrated previously by the disclosures in pending applications referred to above. In fact, a recognition that small molecules having only one reactive group would not result in a secure attachment has led to an improved method disclosed in the present application.

It is clear that currently available immobilization methods suffer from various disadvantages. The present invention provides an improved method especially useful for securely but reversibly anchoring small biomolecules having only one reactive group as well as enzymes or other proteins without compromising their reactivity onto a perfluorocarbon polymer-based carrier.

SUMMARY OF THE INVENTION

The support of this invention contains an attached ligand or binder for the ligand and consists essentially of:

(A) a chemically inert, water immiscible perfluorocarbon carrier having low nonspecific binding to ligands or binders for ligands; and (B) ligand or binder for the ligand securely but reversibly attached to the carrier through an uncharged water soluble polymer to which said ligand or binder for the ligand is attached through covalent bonding and wherein said polymer contains covalently attached perfluorinated anchoring groups for attachment to the carrier.

DESCRIPTION OF THE INVENTION

The support of this invention offers unprecedented advantages in carrying out bioaffinity separations and immunoassays. One of the advantages of using the support of this invention relate to the chemical inertness of the perfluorocarbon carrier. Other known advantages are allowing recovery of scarce or expensive biomolecules for re-use; being stable in an aqueous environment; and permitting re-use of the carrier after removal of the attached water soluble polymer/ligand component.

To perform bioaffinity separations or immunoassays using the support of this invention, the support is prepared by attaching a ligand or a binder for the ligand to a perfluorocarbon carrier. By ligand is meant an antigen, hapten, nucleic acid, enzyme substrate, vitamin, dye or other organic molecules including effectors and inhibitors. By binder for the ligand is meant a molecule capable of binding to said ligand in a specific binding reaction, such as an antibody, enzyme, nucleic acid, binding protein, synthetic mimics of binding proteins such as polylysine and polyethyleneimines, and other biomacromolecules capable of specific binding.

The support must have the ligand or binder for the ligand securely attached to the carrier. By secure attachment is meant an attachment capable of surviving the steps involved in the use of such a solid or liquid support for bioaffinity separations or immunoassays. Secure attachment of the ligand or binder for the ligand is required so as not to contaminate the purified product with desorbed ligands or binders for the ligands, and to prevent loss of the affinity capacity of the support. Prior methods use direct covalent binding of the ligand or binder for the ligand to the carrier to achieve secure attachment. It is highly desirable to be able to recover securely attached ligands or binders when needed. Aside from cost advantages, reversible attachment allows the support to be autoclavable after displacement of the ligands or binders for the ligands by chaotropic agents before re-use. It is also desirable not to alter the inertness of the surface by introduction of reactive groups which can increase nonspecific binding. Further, it is desirable to develop a generic approach can be applicable to a variety of ligands or binders for the ligands.

A general method involving the partition or adsorption technique for preparing perfluorocarbon polymer-based affinity supports is disclosed in pending applications, Ser. Nos. 07/032,642, filed Mar. 31, 1987; and 07/134,026, filed Dec. 17, 1987; and U.S. Pat. No. 4,885,250, issued Dec. 5, 1989 and U.S. Pat. No. 4,954,444, issued Sep. 4, 1990, incorporated herein as reference. In this method, the ligand or binder is modified to permit its selective high affinity (secure) binding to the surface of the perfluorocarbon carrier. The ligand or binder for the ligand is modified by covalently binding perfluorocarbon groups called perfluorinated anchoring groups to the ligand or binder for the ligand either directly or through spacer groups.

The support of this invention contains a perfluorocarbon carrier and a water soluble polymer to which a ligand or binder for the ligand, as well as multiple perfluorinated anchoring groups are covalently attached. By perfluorocarbon is meant a molecule which contains the largest possible, or a relatively large proportion of fluorine atoms in its structure. Perfluorocarbon carriers which can be used to form the support of this invention include various Teflon® fluorocarbon polymers (a registered trademark of E. I. du Pont de Nemours and Company), for example, polytetrafluoroethylene (PTFE), polyvinylfluoride and polyvinylidene difluoride and perfluorodecalin. The carrier can be a solid or liquid, and can be in any form or shape. For example, the carrier can be porous or nonporous microparticles, films, membranes, tubes, or in the form of emulsions. The high mechanical rigidity of certain solid perfluorocarbon carriers allows their use in high pressure liquid chromatography as well as other chromatographic applications. The support can also be used in a batch mode. When the support is in liquid form, it offers additional versatility in that it can be used with counter-current and fluidized bed systems capable of enhancing the binding efficiency of the support.

The support of this invention also contains a water soluble polymer or intermediate linking agent which is covalently attached to a ligand or binder for the ligand and which contains perfluorinated anchoring groups for attachment to the carrier. The water soluble polymer utilized in this invention is either an uncharged hydrophilic polymer such as starch, dextran, agarose, polyethylene glycol, and polyvinyl alcohol containing several reactive groups or a charged polymer which loses its charge during the preparation of the support. It is important to select an uncharged polymer to insure low nonspecific binding. Charged groups on the surface of the support can lead to binding unwanted components from biological samples.

The support of the present invention allows secure attachment of small ligands such as dye molecules, especially those having only one reactive group. The support containing a dye molecule such as a triazine dye having specific affinity for certain proteins can be used for selective purification of proteins. Other supports containing affinity ligands having specificity toward nucleic acids, polysaccharides, or other macromolecules can be prepared similarly for use in various applications.

The perfluorinated anchoring group can contain a reactive group or a group that can be derivatized. By perfluorinated anchoring group is meant a molecule having an alkyl or aromatic group which contains the largest possible or a relatively large proportion of fluorine atoms in its structure. Compounds such as acid chlorides, for example, pentafluorobenzoyl chloride and perfluorooctanoyl chloride, anhydrides, imidazolides, and isocyanate derivatives of various perfluorocarbon acids can be successfully used in the preparation of the support of this invention and are attached to the water soluble polymer through covalent bonding.

The ligand or binder for the ligand, described above, is attached to the water soluble polymer through covalent binding to the reactive groups present in the polymer. The optimal levels of the ligand or binder for the ligand and perfluorinated anchoring groups in relation to the water soluble polymer for secure attachment to the support depend on such factors as the size and nature of the perfluorinated anchoring groups, the ligand or binder for the ligand, the linker group between the perfluorinated anchoring group and the water soluble polymer, if used, and the eventual use of the support.

A preferred method for preparing the support of this invention comprises the following steps:

1) attaching a biomolecule(s) to a preformed water soluble polymeric backbone having multiple reactive groups;

2) introducing multiple perfluorinated anchoring groups to the polymeric backbone; and 3) forming a support by attaching said polymeric backbone having multiple perfluorinated anchoring groups and a biomolecule(s) onto the surface of a perfluorocarbon carrier.

Using the method described above, the biomolecule is securely but reversibly attached to the perfluorocarbon carrier such that it does not leach during use and is recoverable for re-use.

Steps 1) to 3) can be conducted in any order desired. For example, the water soluble polymer can be first substituted with multiple perfluorinated anchoring groups and purified, followed by attachment of a biomolecule, and then reaction with a solid or liquid perfluorocarbon carrier to form the support. In another example, the substituted water soluble polymer can be reacted with a solid or liquid perfluorocarbon carrier first to pre-form the surface having reactive groups, followed by reaction with a biomolecule. The biomolecule can be attached by well known chemical means using the functional groups on the ligand or binder for the ligand or through activated spacers including homo- or bi-functional linking agents.

The method described above can be used for attaching proteins such as an enzyme to a perfluorocarbon carrier without compromising the enzyme's reactivity. A preactivated or derivatized perfluorocarbon carrier can be prepared by anchoring, for example, perfluoroalkyl substituted polyvinyl alcohol onto a PTFE polymer. A portion of the unsubstituted hydroxyl groups on the surface can be reacted with a homo-or bi-functional linking agent capable of forming a chemical bond with a protein. In the final step, an enzyme is added to the derivatized surface to attach it covalently to the perfluoroalkyl substituted polyvinyl alcohol intermediate water soluble polymer. This approach minimizes the exposure of the enzyme to the various reaction steps involved in the preparation of the support and allows the enzyme to retain most of its activity. The support containing an enzyme can be used for various applications such as in enzyme reactors or for biosensor applications. The optimal level of substitution of the water soluble polymer depends largely on the nature and size of the enzyme to be immobilized and the final use of the support.

The examples below exemplify this invention.

EXAMPLE 1

Preparation of Support Containing Triazine Dye

A. Reaction of Triazine Dye with Polyvinyl Alcohol

Five grams of water soluble polyvinyl alcohol (PVA), average MW of 10,000 and 2 grams of a triazine dye, Procion red H-3B, were dissolved with mixing in 100 mL of distilled water. Two mL of 2M sodium hydroxide and 20 mL of a 22% (weight/volume) solution of sodium chloride were added to the above mixture, and the resulting mixture was allowed to react while being stirred for 2 hours at 55° C. The reaction mixture was then allowed to cool to ambient temperature. Analysis by gel filtration followed by thin layer chromatography indicated that a portion of the dye was adsorbed on the polymeric backbone.

The covalently bound polyvinyl alcohol-triazine dye structure was purified as follows. 60 mL of the above reaction mixture was diluted with 200 mL of a solvent mixture consisting of 50 parts of ethylmethyl ketone, 30 parts of 1-butanol, and 20 parts of acetone (by volume) and the mixture shaken with silica (30 g) for 10 minutes. The silica was transferred to a sintered glass filter funnel and repeatedly washed with 0.3-L portions (2L total) of a second solvent mixture consisting of 50 parts of ethylmethyl ketone, 30 parts of water, 30 parts of 1-butanol and 20 parts of acetone (by volume) until the filtrate was colorless. The purified polyvinyl alcohol-triazine dye structure was washed off the silica with 100 mL of water, concentrated by rotary evaporation, and lyophilized. The extent of dye attachment was estimated by dissolving a small weighed amount of the polyvinyl alcohol-dye structure in water, and measuring the concentration of the dye spectrophotometrically. Absorbance was measured at 534 nm for the red dye. The molar ratio of the red dye to polyvinyl alcohol was found to be 1.03.

B. Attachment of Perfluorinated Anchor Group

One part of fresh pentafluorobenzoyl chloride was diluted with 9 parts perfluorodecalin (by volume). One mL of this reaction mixture was mixed with 10 mL of a 1% (w/v) dye-conjugated polyvinyl alcohol in water. The reaction mixture was subjected to rotary tumbling at ambient temperature for a period of 4 hours. The resulting mixture was centrifuged for 5 minutes at 5,000 rpm, the aqueous phase was then removed, rotary evaporated, and lyophilized. The extent of pentafluorobenzoylation of dyed polyvinyl alcohol was estimated by measuring the absorbance at 275 nm of aliquots (diluted 1 to 1000 in water) taken from the hydrophobic perfluorodecalin phase during the reaction. Aqueous solutions of perfluorobenzoyl chloride were used as control. The estimated extent of pentafluorobenzoylation was confirmed by monitoring the disappearance of the hydroxyl groups on the polyvinyl alcohol using a cobaltothiocyanate reagent (D. J. Stewart, "Immobilisation of Triazine Dyes on Inert Hydrophobic Supports for Affinity Chromatography", Ph.D. Thesis, University of Cambridge, 1989).

C. Preparation of Support

Two polyvinyl alcohol-Procion H-3B-PFB conjugates were prepared at two different levels of PFB incorporation. The conjugates were prepared as described above, having a PFB to PVA molar ratio of 28.0 and 52.7, respectively, as determined by absorbance at 275 nm, and a molar ratio of the triazine dye to PVA of 1.03.

Fifty-milligram portions of a Perflex®-35S solid perfluorocarbon chromatographic carrier (a registered trademark of E. I. du Pont de Nemours and Company), were mixed with 1-mL aqueous solutions containing 2 mg/mL of the two conjugates described above, for 4 hours at room temperature with rotary tumbling. Comparision of the intensity of coloration, visually and by absorbance measurement described below, provided a measure of the adsorption of the two conjugates to Perflex®-35S demonstrated that the greater the extent of perfluorocarbon substitution, the stronger the adsorption.

Ten grams of each of the supports thus prepared were washed with 100 mL of distilled water, followed by 50 mL of aqueous (0.1% by weight/volume) Zonyl® FSN fluorosurfactant (a registered trademark of E. I. du Pont de Nemours and Company). The level of adsorption of the conjugates to the carrier and the amount of the triazine dye on each support were determined by measurement of the absorbances at 275 nm and 534 nm, respectively. The support prepared using the conjugate having a PFB to PVA ratio of 28.0 was estimated to contain 21.6 mg conjugate per dry gram Perflex®-35S and 1.36 micromoles dye per dry gram of Perflex®-35S. The support prepared using the conjugate having a PFB to PVA ratio of 52.7 was estimated to contain 29.4 mg conjugate per dry gram Perflex®-35S and 1.40 micromoles dye per dry gram of Perflex®-35S.

Stability of the support of this invention so prepared was evaluated by washing a column packed with support with acids, bases, salts and various organic solvents. Desorption of the conjugates containing the dye ligand was monitored spectrophotometrically using the triazine dye as a detectable entity. The support was determined to be stable in 1M sodium hydroxide, 1M hydrochloric acid and 6M urea. Organic solvents such as methanol and dimethyl formamide caused the desorption of approximately 3 to 5% of the immobilized conjugate from the carrier. Fluorosurfactants such as Zonyl® FSN (1% by weight/volume), and perfluoropolyoxyethylene, and 10 mg/mL human serum albumin also caused an initial desorption of a small amount of the adsorbed conjugate. However, once equilibrium was reached, no further leaching was observed during a continuous run of the columns under such operating conditions. Therefore, a wash step with methanol can be incorporated to insure that no further leaching of a column occur during use.

When a control non-perfluorobenzoylated PVA-triazine conjugate was used to prepare a support, continuous leaching of the conjugate was observed.

EXAMPLE 2

Preparation of Support Containing Triazine Dye-An Alternative Method

A. Reaction of Polyvinyl Alcohol with Perfluorobenzoyl

One gram of polyvinyl alcohol, MW 14,000 (100% hydrolyzed), was dissolved in 100 mL of distilled water, 1 mL of perfluorobenzoyl chloride was added and the mixture was stirred for one hour at room temperature.

B. Attachment of PVA-PFB to Carrier

One hundred grams of Perflex ®-35S was added to the mixture from Step A with stirring. The slurry was washed on a sintered glass filter funnel with 200 mL each of water, acetone, and water again. The product so prepared, referred to as "pre-support", was utilized in subsequent reactions for covalent attachment of ligand or binders for ligands to prepare various supports of this invention.

C. Preparation of Support

1. Attachment of a Dye to Pre-support 1 g of Procion Blue H.B./C.I. Reactive Blue II was dissolved in 20 mL of 2M sodium hydroxide solution. 10 g of the pre-support prepared as described above was added and the mixture was heated to and held at 65° C. for 4 hours. The blue colored support thus prepared was washed with 50 mL each of water, acetone, and water.

2. Attachment of Protein A to Pre-support 5 g of the pre-support, prepared as described above, was washed with 20 mL each of water, acetone, and dry acetone containing 1 mL of pyridine. To this suspension was added 0.5 mL tresyl chloride and, after 10 minutes of stirring, the reaction mixture was filtered and washed with 20 mL each of acetone, water, and aqueous disodium hydrogen phosphate coupling buffer, pH 8.0. This material was then mixed with 10 mL coupling buffer containing 5 mg of Protein A and mixed gently overnight, filtered and washed with water. Prior to use, the support so formed was washed with aqueous Zonyl ® FSN (0.1%, weight/volume). The support biospecifically bound approximately 1 mg human immunoglobulin per gram of support, indicating successful immobilization of the Protein A.

3. Attachment of Trichloro-s-triazine to Pre-support 10 g of the pre-support, prepared as described above, was mixed with 25 mL of 5M sodium hydroxide for 30 minutes and filtered through a sintered glass filter funnel. This material was added to approximately 25 mL 0.5M trichloro-s-triazine in acetone and, after five minutes, was washed with 50 mL each of acetone, a 50:50 mixture by volume of acetone and water, and water. To the support so formed was added 10 mL of a solution of 1M iminodiacetic acid in 2M sodium hydroxide and gently mixed overnight then washed with 50 mL 1M acetic acid, followed by 50 mL water. The support bound approximately 50 micromoles copper (Cu++) per mL of support.

EXAMPLE 3

Preparation of a Liquid Perfluorocarbon Carrier—Based Support Containing Triazine Dye In general, preparation of a liquid support required the use of a two phase solvent system such as a mixture of perfluorodecalin and water. An affinity polymer with C.I. Reactive Blue 4 as ligand was prepared as described in Example 1 using an appropriate dye and adsorbed to the interface of the solvent. The mixture was emulsified to form a stable liquid support in the aqueous phase. The emulsion may also be prepared in the presence of a fluorosurfactant.

Specifically, one mL of perfluorodecalin was added to 19 mL of the saturated aqueous solution containing the affinity polymer, homogenized for 1 minute and then sonicated for 10 minutes. The resulting emulsion was centrifuged at 2,000 rpm for 5 minutes, resuspended in 19 mL distilled water, centrifuged at 7,000 rpm for 5 minutes, re-suspended in 19 mL of aqueous Zonyl ® FSN (0.1%, weight/volume), and with 19 mL of distilled water. The emulsion concentration, i.e., the volume of perfluorodecalin droplets in the totals, was 5% by volume. The amount of affinity polymer adsorbed to the support was approximately 1 to 5 mg of affinity polymer per mL of emulsion and the amount of dye present was approximately 0 to 0.3 micromoles per mL.

EXAMPLE 4

Protein Purification Using a Solid Support

A. Purification of Lactate Dehydrogenase

A commercially available crude preparation of rabbit muscle lactate dehydrogenase (LDH) was diluted with a buffer solution containing 50 mM Tris-HCl, pH 7.3, to a concentration of 1.0–1.2 mg/mL. The diluted solution was then passed through a Sephadex G-25 gel filtration column. Protein level was determined using the standard Bradford assay, *Anal. Biochem.*, 72, 248 (1976), and the specific activity of the enzyme was determined by the disappearance of NADH by measurement of the absorbance at 340 nm, in the presence of the primary substrate, sodium pyruvate.

A 1-mL column was packed with a support as prepared in Example 1 using Procion red H-3B (dye to PVA ratio, 1.03; PFB to PVA ratio, 35.0; 1.71 micromoles of dye per gram of support). The column was washed with the same buffer as that containing the protein preparation to be purified. The buffer also contained 0.05% (weight/volume) of Zonyl ® FSN fluorosurfactant. A second column was also prepared as a control and was packed with support not containing dye in order to evaluate nonspecific binding properties. Five hundred to 600 micrograms crude LDH in 500 microliters was loaded on the column and eluted with 6 mM NADH, an LDH-specific eluent to condition the column. Next, the same column was loaded with more purified LDH. The eluent (6 mM NADH) was capable of recovering over 90% of LDH, a very high recovery, when a purified preparation of LDH was loaded. The control column showed no measurable nonspecific binding of proteins.

When crude LDH with a specific activity of 31 IU/mg was loaded on an affinity column packed with a support of this invention, the purified LDH recovered had a specific activity of 150 IU/mg, resulting in an overall purification factor of 4.8. Total enzyme activity recovered was approximately 71%.

B. Purification of Serum Albumin from Human Plasma

Human plasma and a stock solution of pure human serum albumin (HSA) were diluted with a buffer containing 10 mM sodium acetate, pH 4.0, to approximately 1.0–1.2 mg/mL as described in Example 4A. The albumin content in the diluted plasma was determined using a standard dye adsorption protein assay for albumin. Purification was performed as described in Example 4A utilizing a support as prepared in Example 1, using a chaotropic agent, 0.5M sodium isothiocyanate (NaSCN), as an eluent. (The NaSCN eluent was capable of recovering more than 90% of HSA when purified HSA was loaded.) When diluted plasma containing 1.9 mg protein (61.5% HSA content) was loaded, 0.88 mg of purified protein (HSA fraction; determined to be 86.8% pure) was recovered, resulting in an overall purification factor of 1.4 and recovery of enriched HSA of 46%. Similar results were obtained using a support of this invention containing Procion blue H-B dye.

EXAMPLE 5

Protein Purification Using Liquid Affinity Support

A. Purification of Lactate Dehydrogenase

A liquid affinity support was prepared as described in Example 3 utilizing C.I. Reactive Red 3 (dye to PVA ratio, 1.03; PFB to PVA ratio, 52.7) and was used in a batch mode to purify rabbit muscle LDH. Concentration of the support suspension was 5% by volume and fluorosurfactant level was 0.1% by weight of the aqueous portion. The level of adsorbed PVA was 0.17% by weight of the volume of settled droplets. LDH solution was prepared as in Example 4A and a 0.1-mL aliquot of this solution (containing 530 μg crude LDH, 29.9 IU/mg) was mixed with 5 mL of the support suspension for 5 minutes at ambient temperature. After repeated washing with LDH buffer containing 0.1% Zonyl® FSN fluorosurfactant, the bound LDH was extracted from the support into an aqueous phase with 6 mM NADH eluent. The overall purification factor was 7.5, the LDH had a specific activity of 224 IU/mg. Recovery of the LDH activity was determined to be 92.5%. (The support was recovered for re-use by allowing droplets to settle, removing supernatant, washing with and resuspending in equilibration buffer and removing supernatant after allowing droplets to settle. The washing and resuspension steps were repeated three times.)

B. Purification of Serum Albumin from Human Plasma

Serum albumin was purified from diluted human plasma according to the method of Example 4B. The purified HSA had a purification factor of 1.86 and recovery was determined to be 72.8%.

EXAMPLE 6

Comparison of Supports

A. Preparation of Support of This Invention

A support was prepared using a blue dye, Procion blue H-B, as described in Example 1A.

B. Preparation of Support Outside of This Invention

A ligand was prepared by perfluoroalkylation of Procion Blue MX-R at two available sites using 1H,1H-pentadecafluoroctylamine in a mixed solvent system of dimethylformamide (DMF) and triethylamine. One hundred milligrams Procion Blue MX-R was dissolved in 7.5 mL of dimethyl formamide to which 160 mg 1H,1H-pentadecafluorooctylamine was added. The reaction mixture was stirred at room temperature and monitored for 24 hours by thin layer chromatographic analysis using a system of 2-propanol/ammonia/ethyl methyl ketone, 30:40:30 by volume, until the reaction was complete. The reaction mixture was then lyophilized to volatilize excess perfluorocarbon reagent and dimethyl formamide [Stewart et al., Journal of Biotechnology, Volume 11, 253-266 (1989)]. The perfluoroalkylated ligand so prepared was then adsorbed onto Perflex®-35S.

C. Comparison of the Supports

The stability of the two supports was compared by monitoring desorption of the dye spectrophotometrically at 620 nm. While both supports were stable in solutions such as water, 1M HCl, 1M NaOH, 1M NaCl, 50 mM Tris-HCl, 6 mM NADH and 20 mM sodium acetate, the support outside the scope of this invention was unstable in DMF or in the presence of fluorosurfactants, resulting in desorption of substantially all of the immobilized ligand. A significant portion of the ligand was also displaced from such a support in methanol, acetone and 0.5M NaSCN. In contrast, the support of this invention remained stable under all such conditions.

We claim:

1. A support containing an attached ligand or binder for the ligand consisting essentially of:
   (A) a chemically inert, water immiscible perfluorocarbon carrier having low nonspecific binding to ligands or binders for ligands; and
   (B) ligand or binder for the ligand securely but reversibly attached to the carrier through an uncharged water soluble polymer selected from the group consisting of starch, dextran, agarose and polyvinyl alcohol to which said ligand or binder for the ligand is attached through covalent bonding and wherein said polymer contains multiple covalently attached perfluorinated anchoring groups attached to the carrier.

2. The support of claim 1, wherein said carrier is selected from the group consisting of polytetrafluoroethylene (PTFE), polyvinylfluoride, polyvinylidene fluoride and perfluorodecalin.

3. The support of claim 1, wherein said perfluorinated anchoring group is selected from the group consisting of perfluorinated acid chlorides, perfluorinated anhydrides, perfluorinated imidazolides, and perfluorinated isocyanates.

4. The support of claim 1 wherein said ligand or binder for the ligand is an enzyme.

5. The support of claim 1 wherein the ligand or binder for the ligand is an antigen.

6. The support of claim 1 wherein the ligand or binder for the ligand is a hapten.

7. The support of claim 1 wherein the ligand or binder for the ligand is a nucleic acid.

8. The support of claim 1 wherein the ligand or binder for the ligand is a vitamin.

9. The support of claim 1 wherein the ligand or binder for the ligand is a dye.

10. The support of claim 1 wherein the ligand or binder for the ligand is an antibody.

11. The support of claim 1 wherein the ligand or binder for the ligand is selected from the group consisting of a binding protein and a synthetic mimic of a binding protein.

12. The support of claim 1 wherein the ligand or binder for the ligand is an enzyme substrate.

13. The support of claim 1 wherein the ligand or binder for the ligand is an enzyme effector.

14. The support of claim 1 wherein the ligand or binder for the ligand is an enzyme inhibitor.

15. The support of claim 1 wherein the ligand or binder for the ligand is a biomolecule capable of specific binding.

16. The support of claim 1, wherein there is a linker group between said perfluorinated anchoring group and said water soluble polymer.

17. A process of preparing a support containing an attached ligand or binder for ligand comprising the steps of:
  (A) covalently attaching a ligand or binder for the ligand to an uncharged, water soluble polymer selected from the group consisting of starch, dextran, agarose and polyvinyl alcohol;
  (B) covalently attaching a perfluorocarbon anchoring group to the product of step (A); and
  (C) contacting the product of step (B) with a perfluorocarbon carrier to attach securely but reversibly said ligand or binder for the ligand to said carrier through said perfluorocarbon anchoring group.

18. A process of preparing a support containing an attached ligand or binder for ligand comprising the steps of:
  (A) covalently attaching a perfluorocarbon anchoring group to an uncharged, water soluble polymer selected from the group consisting of starch, dextran, agarose and polyvinyl alcohol;
  (B) contacting the product of step (A) with a perfluorocarbon carrier; and
  (C) covalently attaching a ligand or binder for the ligand to the polymer in the product of step (B) to achieve a secure but reversible attachment of the ligand or binder for the ligand to said carrier.

* * * * *

UNITED STATES PATENT AND TRADEMARK OFFICE
CERTIFICATE OF CORRECTION

PATENT NO. : 5,270,193

DATED : December 14, 1993

INVENTOR(S) : JOHN WILLIAM DELOUCHE EVELEIGH, CHRISTOPHER ROBIN LOWE

It is certified that error appears in the above-identified patent and that said Letters Patent is hereby corrected as shown below:

On title page, item [19] "Eveleigh" should read --Eveleigh, et al--
Item [75] after "John William Delouche Eveleigh" add
--Christopher Robin Lowe--

Signed and Sealed this

Third Day of May, 1994

Attest:

BRUCE LEHMAN

*Attesting Officer*     *Commissioner of Patents and Trademarks*